(12) United States Patent
Leban

(10) Patent No.: US 7,942,809 B2
(45) Date of Patent: May 17, 2011

(54) FLEXIBLE ULTRASONIC WIRE IN AN ENDOSCOPE DELIVERY SYSTEM

(76) Inventor: Stanley G. Leban, New York, NY (US)

(*) Notice: Subject to any disclaimer, the term of this patent is extended or adjusted under 35 U.S.C. 154(b) by 200 days.

(21) Appl. No.: 11/441,632

(22) Filed: May 26, 2006

(65) Prior Publication Data

US 2007/0276255 A1    Nov. 29, 2007

(51) Int. Cl.
*A61B 1/04* (2006.01)
(52) U.S. Cl. .......................... 600/114; 600/437
(58) Field of Classification Search ...... 601/2; 600/114, 600/156, 437
See application file for complete search history.

(56) References Cited

U.S. PATENT DOCUMENTS

| | | | |
|---|---|---|---|
| 4,660,573 A | 4/1987 | Brumbach | |
| 4,791,915 A * | 12/1988 | Barsotti et al. | 601/2 |
| 4,888,746 A * | 12/1989 | Wurster et al. | 367/138 |
| 5,050,585 A | 9/1991 | Takahashi | |
| 5,199,417 A | 4/1993 | Muller et al. | |
| 5,328,365 A * | 7/1994 | Jacoby | 433/29 |
| 5,359,996 A | 11/1994 | Hood | |
| 5,916,147 A * | 6/1999 | Boury | 600/146 |
| 6,165,150 A * | 12/2000 | Banko | 604/22 |
| 6,190,167 B1 * | 2/2001 | Sharp | 433/119 |
| 6,217,588 B1 | 4/2001 | Jerger et al. | |
| 6,371,966 B1 * | 4/2002 | Pierce et al. | 606/166 |
| 6,461,383 B1 * | 10/2002 | Gesswein et al. | 623/6.11 |
| 6,488,639 B1 * | 12/2002 | Ribault et al. | 601/2 |
| 6,572,538 B2 | 6/2003 | Takase | |
| 6,577,042 B2 * | 6/2003 | Lee et al. | 310/317 |
| 6,582,368 B2 | 6/2003 | Holdaway et al. | |
| 6,582,440 B1 | 6/2003 | Brumbach | |
| 6,669,643 B1 * | 12/2003 | Dubinsky | 600/459 |
| 6,679,838 B2 | 1/2004 | Bala | |
| 6,799,729 B1 * | 10/2004 | Voic | 239/102.2 |
| 6,866,663 B2 * | 3/2005 | Edwards et al. | 606/41 |
| 6,869,431 B2 * | 3/2005 | Maguire et al. | 606/41 |
| 6,869,440 B2 * | 3/2005 | Dobak, III | 607/105 |
| 6,872,205 B2 * | 3/2005 | Lesh et al. | 606/41 |
| 6,887,262 B2 * | 5/2005 | Dobak et al. | 607/105 |
| 7,172,552 B2 * | 2/2007 | Wendlandt | 600/114 |
| 2003/0176873 A1 | 9/2003 | Chernenko et al. | |
| 2003/0187324 A1 | 10/2003 | Gatto | |
| 2003/0187383 A1 * | 10/2003 | Weber et al. | 604/22 |
| 2003/0225332 A1 * | 12/2003 | Okada et al. | 600/439 |
| 2004/0138594 A1 | 7/2004 | Sekino et al. | |
| 2004/0204629 A1 * | 10/2004 | Knapp | 600/156 |
| 2005/0038317 A1 * | 2/2005 | Ratnakar | 600/101 |
| 2005/0143730 A1 | 6/2005 | Novak et al. | |
| 2005/0288582 A1 | 12/2005 | Yu et al. | |

OTHER PUBLICATIONS

W. D. Strohm et al., Ultrasonic Tomography by Means of an Ultrasonic Fiberendoscope: Georg Thieme Viriag, Stuttgart—New York; 1980; pp. 241-244.

* cited by examiner

*Primary Examiner* — Long V Le
*Assistant Examiner* — Saurel J Selkin
(74) *Attorney, Agent, or Firm* — Michael J. Feigin, Esq.; http://PatentLawNY.com

(57) ABSTRACT

The flexible ultrasound wire delivered through an endoscope can bend through multiple radii and deliver ultrasonic energy to the business end of the working channel of an endoscope without requiring percutaneous incisions. The flexible ultrasonic wire is wire or fiber that can be flexed in any direction and is connected at one end to an ultrasonic transducer which is connected to an energy delivering device. An insulating layer between the flexible ultrasonic wire and a metallic working channel is non-metallic and resilient and operates to prevent unwanted fragmentation of the device and possible collateral soft tissue injuries.

10 Claims, 3 Drawing Sheets

FLEXIBLE ULTRASONIC WIRE IN AN ENDOSCOPE DELIVERY SYSTEM

BACKGROUND OF THE INVENTION

1. Field of the Invention

The present invention relates to a flexible ultrasonic wire having ultrasound ablation, lithotripsy and/or therapeutic capability at the business (distal) end of an endoscope or micro-fiber endoscope with at least one radius within the working channel during its use.

2. Description of the Prior Art

The use of ultrasound in an endoscope has been shown by U.S. Pat. No. 4,660,573 to Brumbach. The '573 patent discloses a straight ultrasonic lithotripter probe that prevents the lithotripter from clogging due to the fact that the end of the tube which is connected to the transducer extends into the transducer sufficiently so that materials within the tube will be pumped from the operating site through the transducer and out the extending end of the tube. The ultrasonic energy causes a pumping action which keeps the tube clear. The calculi engaging end of the tube is formed with one or more slots such that when the tube extends into the calculi, liquid can enter through such slit and pass through the tube thus preventing the tube from becoming clogged and over heated since the fluid flow is uninterrupted and continues through the probe.

U.S. Patent Publication No. 2003/0187324 to Gatto, discloses an apparatus and method for intraductal ablation. This patent discloses the use of ultrasound in a micro endoscope for purposes of ablating tissue. The acoustic energy is transmitted down the straight probe and resonates around its length.

U.S. Patent Publication No. 2005/0143730 to Novak et al. discloses an RF Cauterization and ultrasonic ablation instrument with multi-hole collar and electrode mounting sleeve.

One major shortfall in the prior art use of ultrasound in an endoscope environment is the inability to flex or curve within the working channel of the endoscope through one or more radii while maintaining delivery of the ultrasonic energy at a level required to ablate or otherwise destroy the calcification or other bone-like substance that is the target of the ultrasound energy.

SUMMARY OF THE INVENTION

It is therefore an aspect of the present principles to provide a flexible wire to be used within an endoscope capable of delivering ultrasonic energy at the business (distal) end thereof while maintaining complete flexibility during use.

It is another aspect of the present principles to provide a flexible ultrasonic micro-wire, delivered through an endoscope that can transmit ultrasonic energy to the tip while maintaining at least one radius of deflection required to reach the predetermined location within a patient through a natural body opening and ductal system, without requiring percutaneous incisions.

These and other aspects of the present principles are achieved with an endoscope delivery system for delivering ultrasound energy having a flexible, metallic, ultrasonic wire disposed within a working channel of an endoscope and having a tip extendable beyond an end of the working channel for delivering ultrasound energy to a predetermined location within a human body, and an insulating non-metallic layer between the flexible ultrasonic wire and an interior metallic surface of a working channel. The working channel with the flexible ultrasonic wire disposed therein is capable of entering the body through a natural body opening/duct, and bending through one or more radii to reach the predetermined location.

An ultrasonic energy source is connected to the flexible ultrasonic wire for generating transverse and longitudinal energy waves and having amplitude, frequency and transverse and longitudinal energy wave adjustment capability. An irrigation/suction channel is disposed adjacent the working channel, and a video channel is disposed adjacent the working channel for enabling visualization of the tip of the flexible ultrasonic wire as it extends beyond the end of the working channel, toward a predetermined target.

According to one aspect of the present principles, the insulating non-metallic layer is disposed on an interior surface of the metallic working channel. According to another aspect, the insulating non-metallic layer is coated on the flexible ultrasonic wire prior to insertion of the same into a metallic working channel.

The tip of the flexible ultrasonic wire is preferably application specific can include, for example, a needle point, a spear point, a spatula, a spoon, a spade or a cannulated configuration. The (amplitude, frequency, and transverse and longitudinal energy wave) frequency is usually fixed thereby fixing the wavelength. Therefore, only amplitude or longitudinal wave energy is varied with power adjustments to compensate for ultrasound energy losses at the tip resulting from increased length and one or more bends in the flexible ultrasonic wire.

According to a further aspect of the present principles, the flexible ultrasonic wire delivered within an endoscope includes an ultrasonic energy source having amplitude, frequency and other wave adjustment capability. The endoscope has a working channel, an irrigation/suction channel, a video channel for enabling visualization of the business end of the endoscope, a flexible ultrasonic wire disposed within the working channel and having one end connected to the ultrasonic energy source and a free business end, and an insulating non metallic layer (when used within a metallic working channel) between said ultrasonic wire and said interior surface of the working channel. The working channel with said ultrasonic wire disposed therein is capable of bending through one or more radii to enable the business end of said ultrasonic wire to reach a predetermined target point within a patient. The operation of the ultrasonic wire to emit ultrasonic energy at the business end of the scope is performed under direct visualization via the video channel.

According to one aspect, the insulating non-metallic layer is disposed on the interior surface of a metallic working channel, while according to another aspect, the insulating non-metallic layer is disposed on the ultrasonic wire prior to insertion of the same into the same metallic working channel of the endoscope.

Other aspects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings wherein like reference numerals denote similar components throughout the views.

DETAILED DESCRIPTION OF PREFERRED EMBODIMENTS

Figure 1:
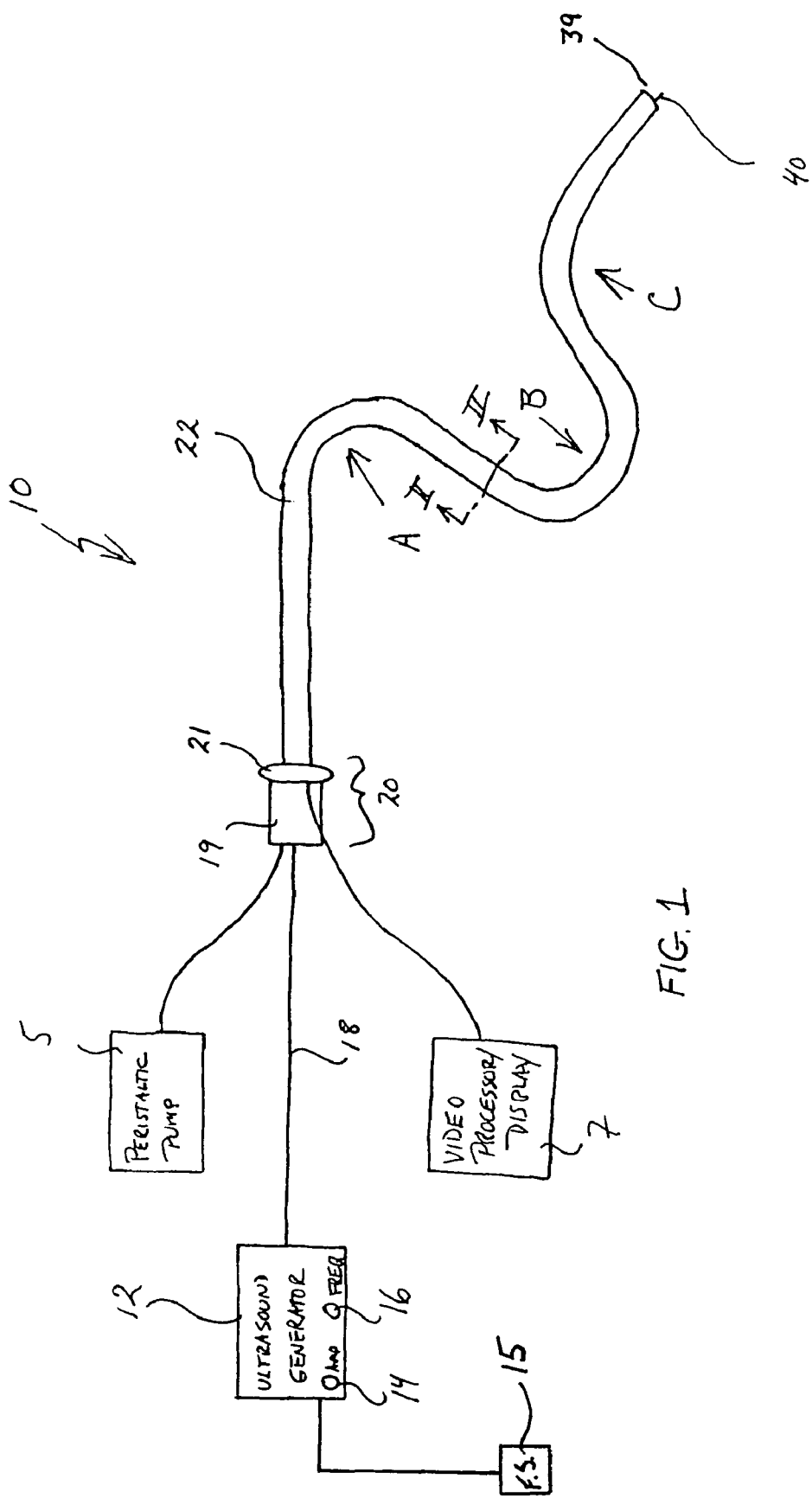
FIG. 1 is plan view of the flexible ultrasound endoscope according to an embodiment of the present principles.

FIG. 1 shows a typical endoscope 10 with an ultrasonic wire according to a preferred embodiment of the present principles. The hand piece 20 is made up of the scope 21 and the ultrasound transducer/horn 19 which are connected in any suitable known manner. The scope 21 is connected to: 1) a video processor/display 7 for providing visualization at the business end 39 of the flexible shaft 22 of the scope 21; 2) a peristaltic pump 5 is connected to the scope 21 to provide irrigation at the business end 39 of the flexible shaft 22; and 3) an ultrasound energy generator 12. The ultrasound generator 12 operates in conjunction with the ultrasound transducer/horn 19 in order to create the ultrasonic longitudinal motion to wire 18. A foot switch 15 can be connected to the ultrasound generator 12 to provide the operator with selective foot operated control during the use of the same.

The ultrasound generator 12 has an electric cable 17 connecting it to the ultrasound transducer/horn 19. The ultrasound wire 18 is connected to the ultrasound transducer/horn 19 and extends into the working channel of the flexible shaft 22 of the scope 21. The micro-wire 18 is flexible and capable of generating ultrasonic energy along its length to be delivered at the business or distal end 40 that extends beyond the end of the flexible shaft 22. According to a preferred aspect of the present principles, the ultrasound generator 12 functions as a power supply for the ultrasound transducer/horn 19.

The sample scope 21 has a flexible shaft 22 that is completely flexible and capable of being manipulated to produce multiple radii of various sizes. When the ultrasonic micro wire 18 is disposed within the working channel and flexed in any direction, a radius A, B, C, etc. is created. Generally speaking, when a wire that transmits ultrasonic energy is flexed, the result is a transverse promulgation of the ultrasonic energy away from the wire 18 in the area of the bend. As such, ultrasonic energy generated by the generator 12 is lost in every flex or bend of the ultrasonic wires contained within the working channel of the scope. Thus, for each flex or bend, an automatic/manual adjustment in the amplitude of the longitudinal wave form, may be required to assist in enabling the longitudinal wave energy of the ultrasonic wire 18 to be transferred to the target for the ultrasound energy (e.g., a stone, or other calcification to be removed using the scope).

Those of skill in the art will recognize that the preferred operating frequency can be dependent upon the particular operation being performed (i.e., the resonant frequency required for the ultrasound energy target) and the length of the wire 18. The length of the wire 18 is generally dependent on the operation being performed and corresponds generally with the frequency wavelength. The amplitude adjustments required to deliver the appropriate longitudinal energy to the target operate to "tune" the system. This tuning results in an automatic elimination of undesirable transverse movement of the wire in favor of the longitudinal energy.

The energy to be delivered by the system of the present principles is preferred to be in a longitudinal fashion. Those of skill in the art will recognize that other variations of energy delivery may be employed without departing from the spirit of the present principles.

Figure 2:
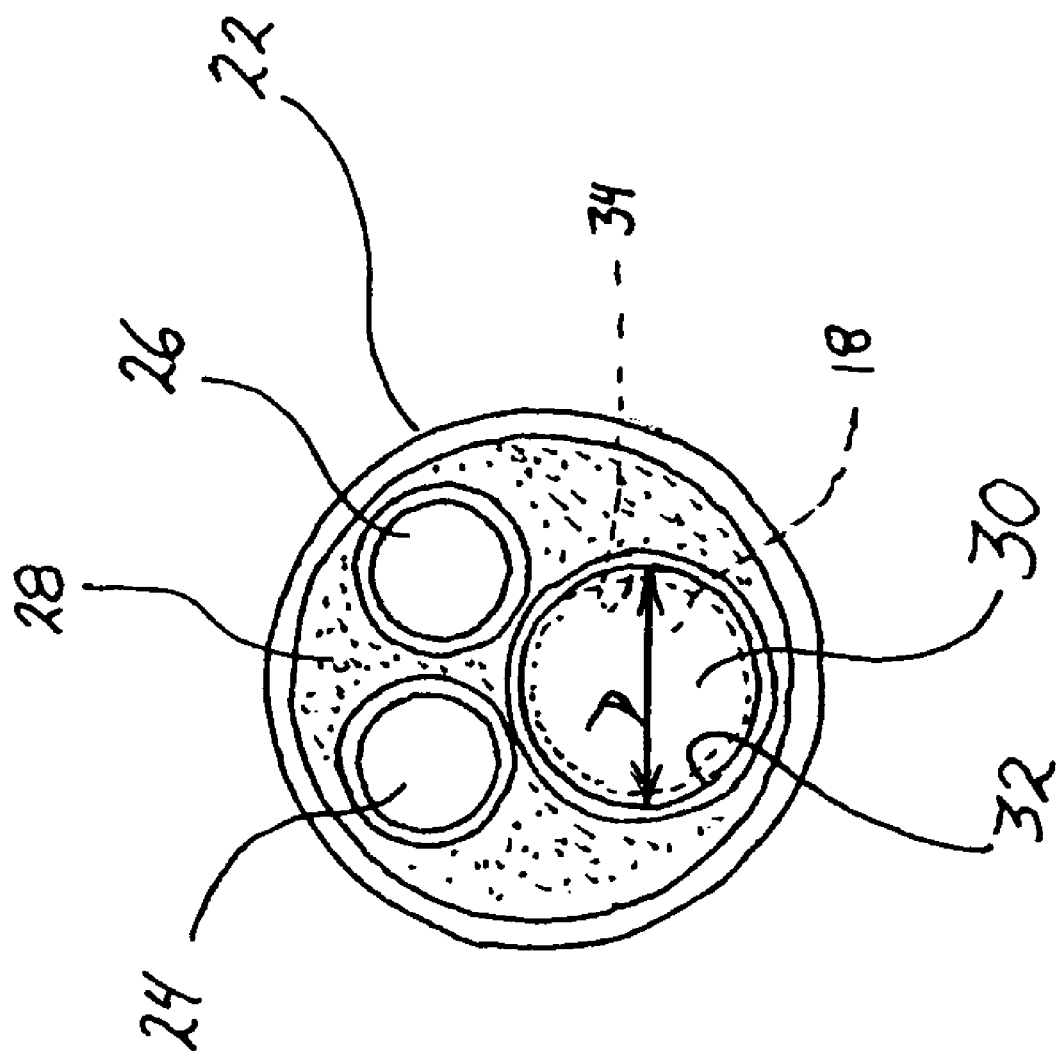
FIG. 2 is a cross-section view of the endoscope of FIG. 1 taken along lines II-II thereof.
Figure 3:
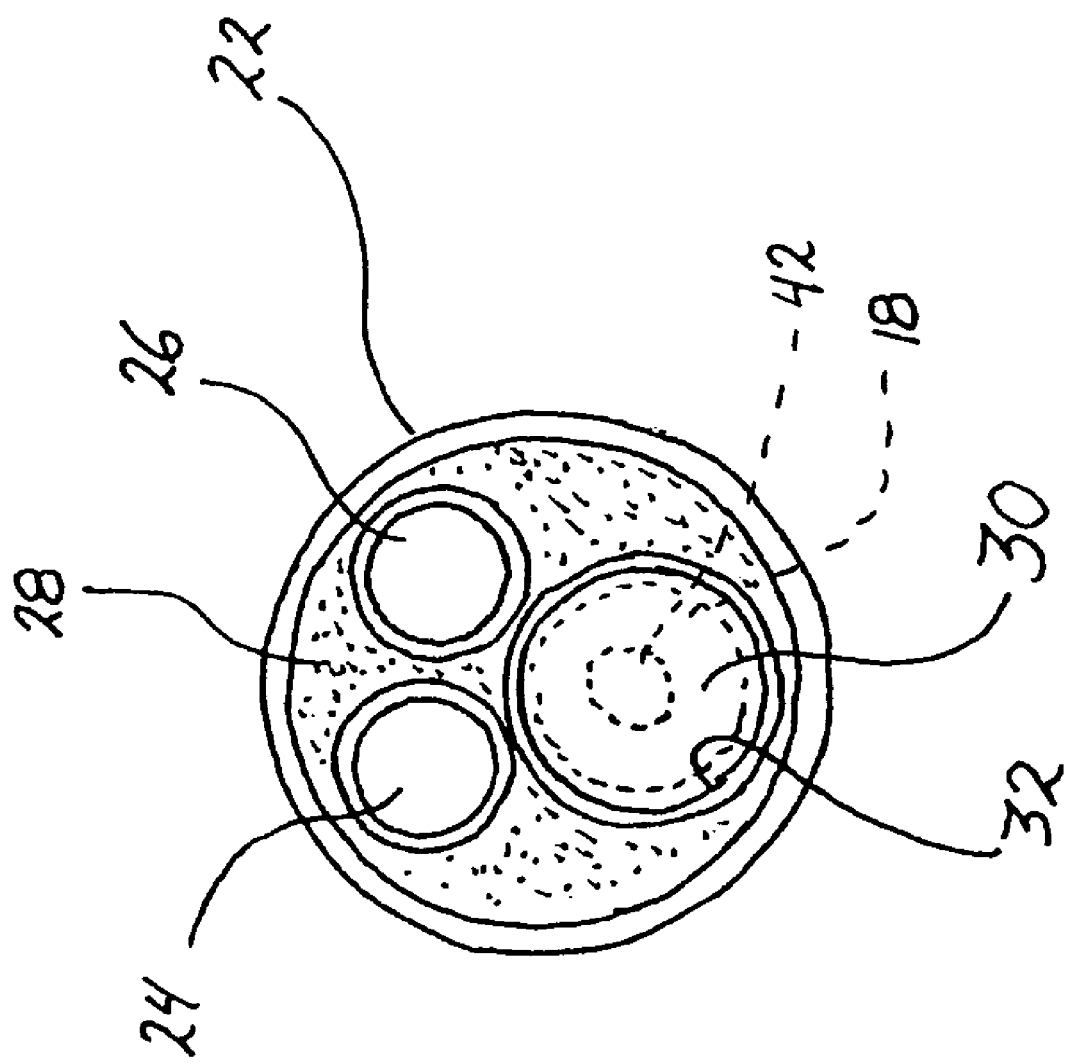
FIG. 3 is s cross-section view of and endoscope according to another embodiment of the present principles.

Referring to FIGS. 2 and 3, there is shown a cross-sectional view of the flexible tube 22 of the endoscope 21. Generally, there are three passageways in the flexible tube 22 of the scope 21. An irrigation channel 24, which is connected to the peristaltic pump 5 (shown in FIG. 1, this channel is alternately used as a suction channel), a video channel 26 for obtaining and carrying video signals at the business end 39 of the scope to the video processor/display device 7 within an operating environment. The largest channel is generally the working channel 30. The working channel 30 has many applications, and according to the present principles, ultrasonic wire 18 is disposed within the working channel 30. A plurality of fiber optics 28 are interspersed around the channels 24, 26 and 30 to provide lighting at the business end 39 of the scope flexible tube 22. Fiber optics 28 enables sufficient light to provide proper visualization at the business end 39 of the scope 21.

According to a preferred aspect of the present principles, the when the scope is metallic in nature, the interior surface 32 of the working channel, or the exterior surface of the ultrasonic wire 18 must be coated or lined with a non-metallic substance. When operating an ultrasonic wire 18 as proposed by the present principles, the exterior surface of the wire itself cannot come into contact with any metallic surface of any kind from the its point of origin at generator 12, all the way through the working channel 30 so that the tip 40 is the only point at which the ultrasonic energy can be delivered from the wire. In the event an energized wire 18 comes into contact with a metallic surface or substance between the generator 12 and the tip 40, the wire would likely shatter, and destroy itself as well as risking collateral tissue damage. As such, the non metallic coating or lining of the interior surface 32 of the working channel 30 will prevent any of these phenomena.

Alternatively, the ultrasonic wire 18 may include a resilient, non metallic coating 34 of any suitable known type, on the exterior surface there of. Examples of such coatings can be silicon, polyethylene, polyamid and the like (in the form of sleeve or permanent coating). Those of skill in the art will recognize that the ultrasonic wire 18 can be made of any suitable known type of metallic material, such as, for example, Titanium, Stainless Steel, or any other suitable metal that can be used for the present applications.

As shown in FIGS. 2 and 3, the working channel 30 has a diameter D that can vary depending on the particular scope 21 and/or the particular application for which the scope is being used. In order to accommodate varying working channel diameters for different applications, the ultrasonic wire 18 can be provided in various gauges, such as 0.39 mm, 0.5 mm, 0.79 mm and so on. These gauge values are given for exemplary purposes only and can be changed without departing from the spirit of the present principles.

The length of ultrasonic wire 18 can be almost any length depending on the overall length of the endoscope being employed, provided that appropriate adjustments of the amplitude and frequency of the ultrasound generator 12 can be made to compensate for any losses in energy resulting from multiple radii bends in the working channel of the scope. The adjustment is to frequency determines the wavelength and thereby allows for incremental increases in the length of the ultrasonic wire 18. The irrigation/suction channel 24 will follow the over all length of the working channel through which the ultrasonic wire 18 will pass through.

FIG. 3 shows another embodiment where ultrasonic wire 18 includes a concentric hole or channel 42. In accordance with this embodiment, channel 42 may be integrated into the wire 18 to provide irrigation/suction. This cannulated embodiment can provide a separate irrigation channel, allowing for the irrigation/suction channel of the endoscope, through which it passes, to be used for suction only. Thus, the efficiency of the combined entities would reduce the time required to perform the particular operation.

The flexible ultrasonic wire/endoscope delivery system of the present principles has unlimited applications in various aspects of medical and surgical treatments. Some examples of contemplated applications are: 1) Flexible endoscopic Intra Corporeal Lithotripsy through natural body channels (i.e., no percutaneous invasions); 2) Flexible endoscopic delivery of ultrasound to promote healing; and 3) Flexible endoscopic-ultrasound delivery to ablate soft tissue lesions. Although this list is not exhaustive, it will be clear to those skilled in the art, that the ability to deliver pin point ultrasound energy to just about any point within the human body while using natural body openings only, provides an advantage over all existing endoscopes that require percutaneous incisions which are significantly more invasive.

While there has been shown, described and pointed out fundamental novel features of the invention as applied to preferred embodiments thereof, it will be understood that various omissions, substitutions and changes in the form and details of the methods described and devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed, described or suggested form or embodiment as a general matter of design choice. It is the intention, therefore, to be limited only as indicated by the scope of the claims appended hereto.

What is claimed is:

1. A delivery system for delivering ultrasound energy, comprising:
   a flexible, metallic, ultrasonic wire disposed within a working channel of an endoscope, said wire extending beyond an end of the working channel for flexibly delivering ultrasound energy to an anatomic target within a human body;
   an insulating non-metallic layer between said flexible ultrasonic wire and an interior metallic surface of the working channel of the endoscope; and
   an ultrasonic energy source connected to the flexible ultrasonic wire, said energy source generating longitudinal ultrasonic energy waves and producing a first amplitude and frequency of said ultrasonic energy beyond said end of said working channel;
   wherein said endoscope working channel with said flexible ultrasonic wire disposed therein comprises a plurality of radii to reach the anatomic target and, at the time of formation of each radius of said plurality of radii, said energy source is configured to adjust said ultrasonic energy waves to provide ultrasonic energy at the tip of the wire to compensate for loss of said first amplitude and frequency when the tip is extended beyond an end of the working channel.

2. The delivery system of claim 1, wherein said insulating non-metallic layer is disposed on an interior surface of said working channel.

3. The delivery system according to claim 1, wherein said insulating non-metallic layer is coated on the flexible ultrasonic wire prior to insertion into the working channel.

4. The delivery system according to claim 1, wherein said amplitude and frequency adjustments compensate for ultrasound energy losses at the tip of the wire resulting from increased length and one or more bends in the flexible ultrasonic wire.

5. A system comprising:
   an ultrasonic energy source having amplitude, and frequency adjustment capability;
   a flexible ultrasonic wire disposed within a working channel of an existing endoscope and having one end connected to the ultrasonic energy source and a free business end; and
   an insulating non-metallic layer between said ultrasonic wire and an interior surface of a working channel of an endoscope;
   wherein said working channel with said ultrasonic wire disposed therein is capable of bending through one or more radii to enable the business end of said ultrasonic wire to reach an anatomic target within a patient to provide ultrasonic energy at the free business end of the flexible wire when the free business end is extended beyond an end of the working channel, and
   wherein the ultrasonic energy source is configured to produce ultrasonic energy, said energy compensating for a plurality of bends through said radii, at the time of formation of each of said bends.

6. The system according to claim 5, wherein said insulating non-metallic layer is disposed on the interior surface of the working channel.

7. The system according to claim 5, wherein said insulating non-metallic layer is disposed on said ultrasonic wire prior to insertion into the working channel of the endoscope.

8. The system according to claim 5, wherein said working channel of the existing endoscope is configured to enters the body of a patient through a natural body opening.

9. A method of delivering ultrasonic energy through a bendable endoscope, said method comprising:
   providing a first amplitude and wavelength of said ultrasonic energy at a business end of said endoscope;
   bending said endoscope around a plurality of radii within a human body;
   determining a change in amplitude and wavelength of said ultrasonic energy at said business end resulting from said bending of the endoscope; and
   at a source of said ultrasonic energy, adjusting said amplitude and wavelength of said ultrasonic energy to compensate for said change in amplitude and wavelength at the time of formation of each bending.

10. The method of claim 9, further comprising steps of:
    bending said endoscope around a second radius within the human body; and
    at the source of said ultrasonic energy, adjusting said amplitude and wavelength of said ultrasonic energy to compensate for said second bending.

* * * * *